(12) United States Patent
Pipe (10) Patent No.: US 12,274,543 B2
(45) Date of Patent: Apr. 15, 2025

(54) METHOD FOR SEPARATING DYNAMIC FROM STATIC SIGNALS IN MAGNETIC RESONANCE IMAGING

(71) Applicant: Mayo Foundation for Medical Education and Research, Rochester, MN (US)

(72) Inventor: James G. Pipe, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 188 days.

(21) Appl. No.: 17/796,456

(22) PCT Filed: Jan. 29, 2021

(86) PCT No.: PCT/US2021/015616
§ 371 (c)(1),
(2) Date: Jul. 29, 2022

(87) PCT Pub. No.: WO2021/155089
PCT Pub. Date: Aug. 5, 2021

(65) Prior Publication Data
US 2023/0052832 A1  Feb. 16, 2023

Related U.S. Application Data

(60) Provisional application No. 62/967,763, filed on Jan. 30, 2020.

(51) Int. Cl.
*A61B 5/055* (2006.01)
*G01R 33/20* (2006.01)

(52) U.S. Cl.
CPC .............. *A61B 5/055* (2013.01); *G01R 33/20* (2013.01)

(58) Field of Classification Search
CPC ............................. G01R 33/20; G01R 33/567; G01R 33/56509; A61B 5/055
See application file for complete search history.

(56) References Cited

U.S. PATENT DOCUMENTS

2007/0098298 A1* 5/2007 Xiang ................ G01R 33/4828
382/128
2007/0238972 A1 10/2007 Nauerth
(Continued)

FOREIGN PATENT DOCUMENTS

EP        1816485 A2   8/2007
WO    2021155089 A1   5/2021

OTHER PUBLICATIONS

International Search Report of related PCT/US2021/015616, mailed on May 26, 2021, 3 pages.
(Continued)

*Primary Examiner* — Amelie R Davis
(74) *Attorney, Agent, or Firm* — Quarles & Brady LLP (57) ABSTRACT

Described here are systems and methods for separating magnetic resonance signals that are changing over a scan duration (i.e., dynamic signals) from magnetic resonance signals that are static over the same duration. As such, the systems and methods described in the present disclosure can be used to remove artifacts associated with dynamic signals from images of static structures, or to better image the dynamic signal (e.g., pulsatile blood flow or respiratory motion).

20 Claims, 5 Drawing Sheets

(56) References Cited

U.S. PATENT DOCUMENTS

2015/0371372 A1* 12/2015 Athavale .............. A61B 5/055
          382/131
2016/0091584 A1*  3/2016 Feiweier ............. G01R 33/543
          324/309
2019/0346522 A1* 11/2019 Botnar ............... G01R 33/5676

OTHER PUBLICATIONS

Written Opinion of related PCT/US2021/015616, mailed on May 26, 2021, 11 pages.

Ehman, R. L., et al. "Adaptive Technique For High-Definition Mr Imaging Of Moving Structures", Radiology, Radiological Society of North America, Inc, US, vol. 173, No. 1, Oct. 1, 1989 (Oct. 1, 1989), pp. 255-263, XP009050015, ISSN: 0033-8419.

Zaitsev, M., et al.: "Motion artifacts in MRI: A complex problem with many partial solutions : Motion Artifacts and Correction", Journal of Magnetic Resonance Imaging, vol. 42, No. 4, Jan. 28, 2015 (Jan. 28, 2015), pp. 887-901, XP055433888, US ISSN: 1053-1807, DOI: 10.1002/jmri.24850.

Bailes, D. R., et al. "Respiratory Ordered Phase Encoding (ROPE): A Method For Reducing Respiratory Motion Artefacts In MR Imaging", Journal of Computer Assisted Tomography, New York, NY, US, vol. 9, No. 4, Jul. 1, 1985 (Jul. 1, 1985), pp. 835-838, XP000653665.

Vergeldt, F. J., et al. "Multi-component quantitative magnetic resonance imaging by phasor representation", Scientific Reports, vol. 7, No. 1, Apr. 13, 2017 (Apr. 13, 2017), pp. 1-10, XP055801837, DOI: 10.1038/s41598-017-00864-8.

Tsao, J., et al. k-t BLAST and k-t SENSE: Dynamic MRI with High Frame Rate Exploiting Spatiotemporal Correlations. Magn Reson Med. 2003;50(5):1031-42.

Hansen, M., et al. k-t BLAST Reconstruction from Non-Cartesian k-t Space Sampling. Magn Reson Med. 2006;55(1):85-91.

Muthurangu, V., et al. Real-time Assessment Of Right And Left Ventricular Volumes And Function In Patients With Congenital Heart Disease By Using High Spatiotemporal Resolution Radial k-t SENSE. Radiology. 2008;248(3):782-91.

TSAO,J., et al. MRI Temporal Acceleration Techniques. J Magn Reson Imaging. 2012;36(3):543-560.

Feng, L., et al. Highly Accelerated Real-Time Cardiac Cine MRI Using k-t SPARSE-SENSE. Magn Reson Med. 2013;70(1):64-74.

Paul, J., et al. High-Resolution Respiratory Self-Gated Golden Angle Cardiac MRI: Comparison of Self-Gating Methods in Combination with k-t SPARSE SENSE. Magn Reson Med. 2015;73(1):292-8.

Barth, M., et al. Simultaneous Multislice (SMS) Imaging Techniques. Magn Reson Med. 2016;75(1):63-81.

Anderson III, A. G., Wang, D., & Pipe, J. G. (2020). Controlled aliasing for improved parallel imaging with a 3D spiral staircase trajectory. Magnetic Resonance in Medicine, 84(2), 866-872.

Anderson III, A. G., Wang, D., & Pipe, J. G. (2019). Improved parallel imaging with a 3D spiral staircase trajectory. In Proceedings of the 27th Annual Meeting of ISMRM, Montréal, Québec, Canada (p. 2408).

Pipe, J. G., et al. Effects of Interleaf Order for Spiral MRI of Dynamic Processes. Magn Reson Med. 1999;41(2):417-22.

* cited by examiner

FIG. 7

METHOD FOR SEPARATING DYNAMIC FROM STATIC SIGNALS IN MAGNETIC RESONANCE IMAGING

CROSS-REFERENCE TO RELATED APPLICATIONS

This application represents the national stage entry of PCT/US2021/015616 filed on Jan. 29, 2021 and claims the benefit of U.S. Provisional Patent Application Ser. No. 62/967,763, filed on Jan. 30, 2020, and entitled "METHOD FOR SEPARATING DYNAMIC FROM STATIC SIGNALS IN MAGNETIC RESONANCE IMAGING," the contents of which is herein incorporated by reference in its entirety.

BACKGROUND

In magnetic resonance imaging ("MRI"), there are many methods for multi-band imaging, which may also be called simultaneous multi-slice ("SMS") MRI. Applied to multi-shot spiral MRI, the basic principle is that multi-shot data can be collected from two or more slices at the same time by applying a relative phase shift to the spiral arms for each slice. This relative phase shift is then changed with each shot.

With no special reconstruction, the two (or more) images would superimpose in a standard image. If, however, the phase applied for a particular slice is removed from each arm of the collected data corresponding to that slice, coherent images of that slice can be reconstructed. In these images, the signal from the other slice will appear as an incoherent artifact. With data from multiple coils, the phase and magnitude information inherent in each coil image can be used to fully separate the two data sets using algorithms such as iterative SENSE. The nature of these incoherent artifacts is notable. If the artifacts from the "contaminating" slice are spread across the images sufficiently, then the information from each slice is sufficiently orthogonal across all the coils, such that this signal separation can be done with minimal artifact and effectively no noise (or SNR) penalty.

As noted above, SMS MRI can be implemented with more than two slices. The number of slices combined in such a manner is referred to by an SMS acceleration factor, "R." With large R, the artifact suppression will start to decrease, and the g-factor (noise) will increase. The degree of this effect depends on how orthogonal the entire set of slices can be made, given the relative phase modulation of each slice and the coil sensitivities.

When collecting data using spiral MRI, any signal that changes over time during the scan will typically create image artifacts. For example, with a conventional linear collection of spiral arms (in which data are acquired from linearly ordered spiral trajectories), ring-like structures will appear around dynamic signal sources, such as blood vessels, due to the periodic oscillation of the signal magnitude and phase in k-space. Changing the temporal order of the spiral arms, and thus the expression of that oscillating signal in k-space, can more incoherently spread the artifact across the image.

SUMMARY OF THE DISCLOSURE

The present disclosure addresses the aforementioned drawbacks by providing a method for reconstructing an image from magnetic resonance data, in which static and dynamic signal components in the magnetic resonance data have been separated. Magnetic resonance data are accessed with a computer system. The magnetic resonance data include k-space samples acquired from a subject with an MRI system in a plurality of different shots over a duration of time. Temporal position data are determined, in which the temporal data define, for each of the plurality of shots, the temporal positions at which k-space samples were acquired relative to the duration of time. Phase-modified data are generated by weighting the k-space samples acquired in each of the plurality of different shots by a corresponding phasor that is constructed based in part on the temporal position corresponding to that given shot. One or more images are then reconstructed from the magnetic resonance data and the phase-modified data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIGS. 1A-1D show example images from a digital phantom study.

DETAILED DESCRIPTION

Described here are systems and methods for separating magnetic resonance signals that are changing over a scan duration (i.e., dynamic signals) from magnetic resonance signals that are static over the same duration. As such, the systems and methods described in the present disclosure can be used to remove artifacts associated with dynamic signals from images of static structures, or to better image the dynamic signal (e.g., pulsatile blood flow or respiratory motion). Among other uses, the systems and methods described in the present disclosure allow for the removal of motion artifacts from static images. Additionally or alternatively, images of time-varying signals can be generated with little to no signal-to-noise ratio loss, and without much increase in scan time.

The systems and methods described in the present disclosure can be referred to as Temporal Harmonic Encoding and Separation in Space ("THESIS"), and are applicable to a number of different imaging techniques, including Cartesian and non-Cartesian (e.g., spiral) imaging. In general, oscillatory signals are either coherently displaced or scattered incoherently in an image of static signal through the choice of repetition time ("TR") and shot ordering (e.g., phase encoding order, spiral arm order). This spectral orthogonalization allows for the signal sources (e.g., static versus various harmonics of the oscillation) to be separated based on coil sensitivities, thereby resulting in a framework for separation of static from harmonic signals.

In some implementations, THESIS can purposefully impose coherent spatial separation of signals, which occurs for signal changes from periodic motion in order to enable separation of signals in conventional imaging.

Additionally or alternatively, THESIS can purposefully impose incoherent spatial separation of signals, which occurs for signal changes from periodic motion, in order to enable separation of signals in spiral or other imaging techniques. For instance, when MRI signals from two sources (e.g., slices) have appropriate relative (and changing) differences in phase applied between each shot, these two source signals can be fully separated with minimal artifact and minimal noise penalty. As an example, for spiral MRI, when the phase for any single source (e.g., slice) is removed to make that source coherent, this applied phase will make the signals from the other sources (e.g., slices) spread incoherently across the image (and therefore across the coil sensitivities), making the signals from the multiple sources orthogonal. With knowledge of the periodicity, or time-course, of a time-varying signal, that signal can be modulated such that it is incoherently spread across the image of the static signal. By combining these findings, methods for separating dynamic and static signals can be provided.

As noted, the systems and methods described in the present disclosure are capable of separating static and dynamic signal components. In this way, images can be reconstructed to separately depict these static and dynamic signals. As a result, one advantage of the systems and methods described in the present disclosure is the removal of artifacts due to pulsatile flow, respiration, cardiac motion, or other physiological, cyclical, or periodic motion sources. This provides an improvement over prior approaches of binning for cardiac or respiratory gating.

In some instances, the methods described here can be combined with temporal binning for SD imaging, such as binning over the respiratory cycle and applying the methods described in the present disclosure over the cardiac cycle. Additionally or alternatively, the methods can be combined with binning over the same cycle, such as by generating dynamic signal components that can be used to fill in missing data with a binning procedure.

As another advantage, the systems and methods described in the present disclosure can be used to separate out modulating Bo effects. As a result, more effective deblurring can be achieved for imaging techniques such as spiral MRI. In this way, improvement for clinical applications such as spine imaging during respiration can be provided.

The dynamic signal components that can be separated may also include separating signals that are applied in a periodic fashion, such as oscillations in magnetic resonance elastography ("MRE"), magnetization transfer (e.g., via applying RF pulses with constant flip angles, but oscillating energy), or arterial spin labeling ("ASL") tagging (e.g., via oscillatory saturation of arterial supply). This can provide improvements that enable rapid, robust quantitative imaging in many cases.

The systems and methods described in the present disclosure can also be applied in instances where there is an exponentially decaying signal over an echo train, such as for MP-RAGE or TSE/FSE/RARE. In these applications, that changing signal can be removed (or at least partially removed) to improve image quality in the final image, without needing additional scan time and without an SNR penalty. Advantageously, this may enable quantification of the rate (e.g., T1 or T2) at which that signal is decaying, adding a quantitative aspect to otherwise conventional images.

As noted above, oscillatory signals can be made to be incoherent in an image of static signal. This provides a synergy with the other finding describe above, in which two (or more) signals can be separated when either is spread incoherently across an image that is designed to coherently represent the other signal.

For THESIS, the signal can be modeled as, $$S(x, t) = \sum_{n=-\infty}^{n=+\infty} S_n(x) e^{i 2\pi n \frac{t}{T}}; \quad (1)$$

where $S_n$ is the spatial distribution of signal at the nth harmonic, t is the time the data are sampled, and T is the period of the base harmonic (n=1). In practice the harmonics considered will be a small subset (e.g., |n|<N). The phasor in the summation can resemble the phasor used in Fourier transform, and so (discretizing x) the DFT of the signal can be written as, $$s(k) = \sum_{k=0}^{K-1} \sum_{n=-\infty}^{n=+\infty} S_n(x) e^{i 2\pi \left[ n \frac{t(k)}{T} + k \frac{x}{X} \right]}. \quad (2)$$

Recognition of how the phase for each harmonic can be combined with the Fourier encoding phase allows the spatial encoding of the harmonics to be controlled (e.g., whether coherent or incoherent). As described below, this technique can be applied in a number of different applications, including spiral imaging (i.e., Spiral THESIS), Cartesian imaging (i.e., Cartesian THESIS), and synthetic THESIS (SynTHESIS).

Figure 1A:
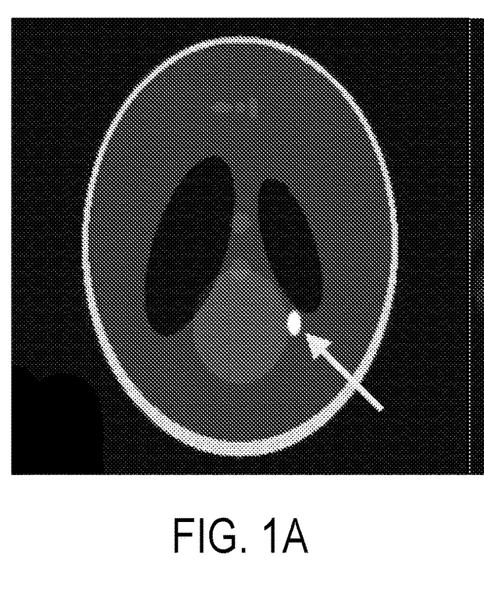
FIG. 1A shows a digital phantom composed of a static Shepp Logan phantom and a sinusoidally varying ellipse (yellow arrow). When used to synthesize spiral MRI data, the digital phantom results in an image (FIG. 1B) where the static signal is coherent but the oscillatory ellipse is incoherently distributed across the image. Multiplying the k-space data by a phase for each arm (FIG. 1C, inset shows color legend for phase) that corresponds to the cycle of the ellipse's signal, results in an image (FIG. 1D) for which the static image is spread incoherently across the image, and (some part of) the ellipse shows up coherently.
Figure 1B:
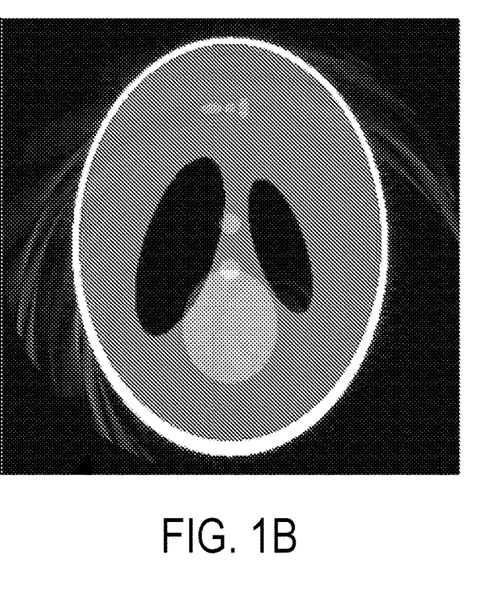

FIGS. 1A-1D show results from simulated data. FIG. 1A shows a digital phantom that is the combination of a static Shepp Logan image and an ellipse with sinusoidally varying signal (yellow arrow) that is proportional to sin(t/T), where T is the period of the varying signal. When MR data are synthesized for spiral k-space trajectories, a conventional reconstruction produces an image (FIG. 1B) for which the Shepp Logan phantom is seen coherently, and the oscillating signal from the ellipse is expressed as a widely distributed incoherent artifact.

Prior to conventional reconstruction, the phasor in Eqn. (1) can be removed for the nth harmonic by multiplying each spiral arm by exp(−i2πn(t/T)), whose phase (FIG. 1C) corresponds to the time, t, during the period, T, at which each respective spiral arm is collected. After this is done, conventional reconstruction from these phase modified data produces an image (FIG. 1D) for which the static image is spread incoherently, and the sinusoidally varying object appears coherent. A similar (complementary) image can be obtained by using the conjugate phasor for the n=−1 harmonic, exp(i2πn(t/T)).

Figure 1C:
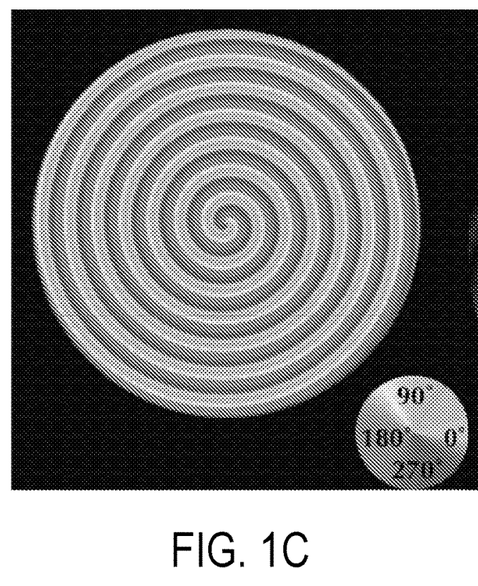
Figure 1D:
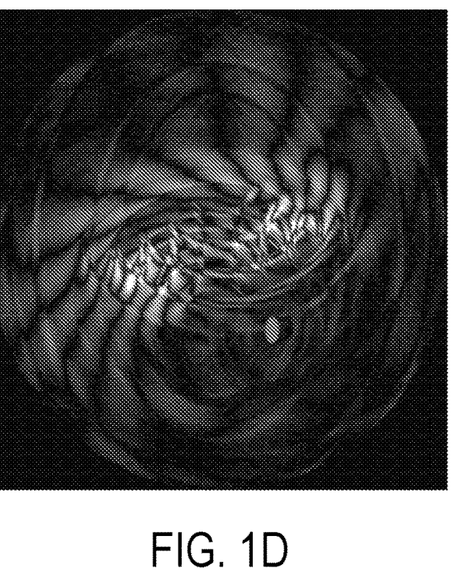

In this way, the image reconstructed from the original data and the image, or images, reconstructed from the phase modified data can be viewed similarly to those from simultaneously excited slices as described above. Thus, the two signals (static and time-varying) are separable similar to signals from two or more simultaneously excited slices.

Figure 2:
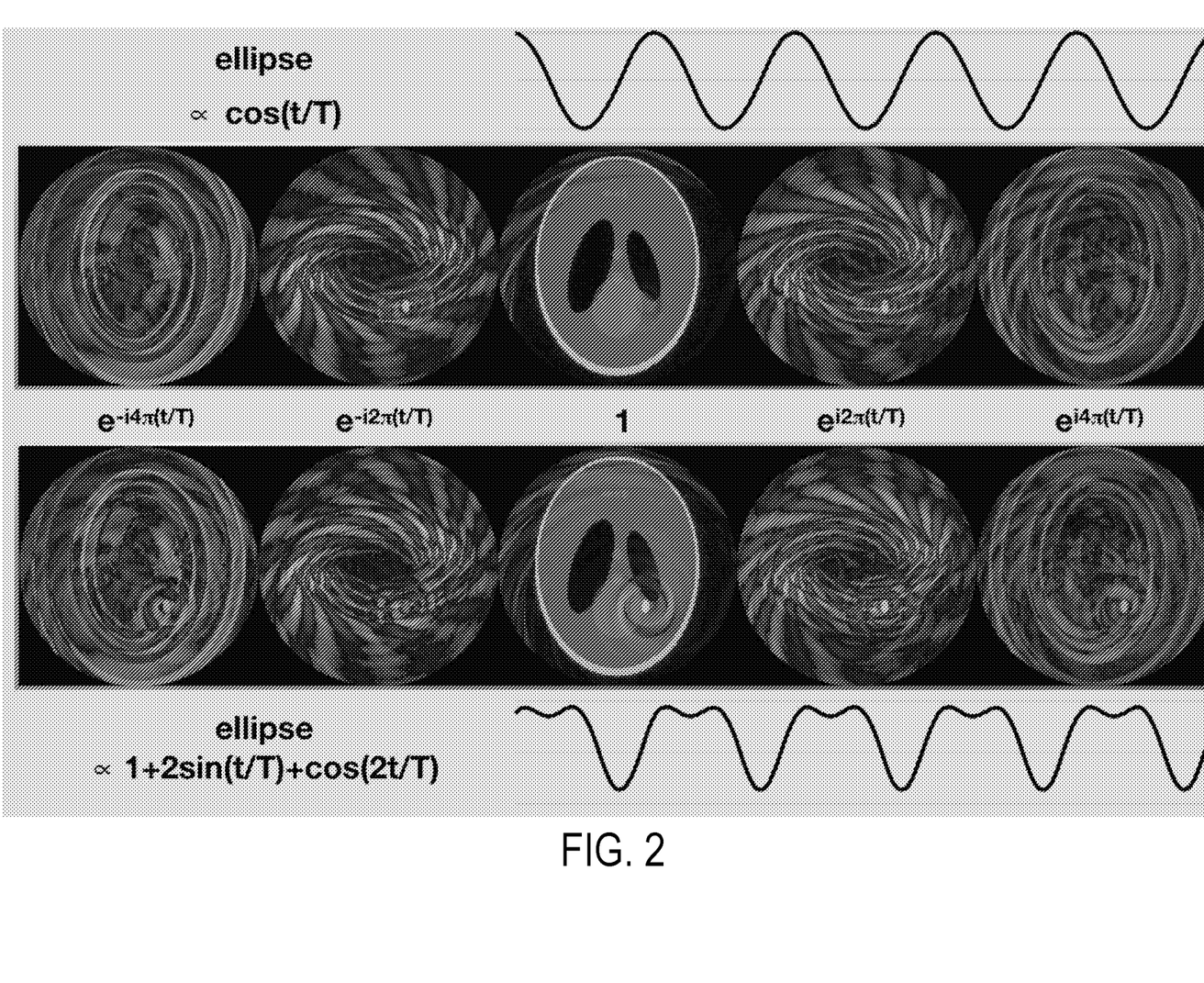
FIG. 2 shows an extension of the digital phantom example shown in FIGS. 1A-1D, with waveform and 5 harmonic images for (top) a sinusoidal elliptical signal (similar to FIGS. 1A-1D), and (bottom) a more complicated 5-harmonic elliptical signal. The top image, with signal given by cos(t/T), shows a coherent ellipse in the positive and negative first harmonic. The bottom image shows a positive ellipse in the 0th harmonic (static), ellipses with +/−π/2 phase in the positive and negative first harmonic (sine wave), and positive ellipses in the positive and negative second harmonic (cosine wave).

The process described above is linear, such that if the dynamic portion of the image (e.g., the ellipse in the digital phantom example) has a static component and a second harmonic, then each component can be made coherent with the use of appropriate phases, as shown in FIG. 2. The number of harmonics is comparable to the number of combined slices in an SMS acquisition, and so can be referred to as the factor, "R."

FIGS. 1A-D and 2 illustrate that removing a phasor from the nth harmonic of Eqn. (1) can be used to create a coherent imaging of $S_n$; however, in those instances the remaining signal from other harmonics can still be present in the image (and expressed incoherently). A process such as an appropriately modified iterative SENSE algorithm, such as the one illustrated in FIG. 3, can be used to fully separate them.

To separate multiple harmonics with low noise amplification and low artifact, each should be encoded orthogonally, such as via a combination of the coil sensitivities and the respective point spread functions ("PSFs"). The PSF, which is a mathematical description of the distribution of signal from any of the sources in these reconstructions, can be controlled by the order in which spiral arms are collected relative to the changing signal. The temporal order in which arms are collected, $t_{arm}$, for spiral MRI can distribute the applied harmonic phases, exp(i2πn($t_{arm}$/T)), across shots so that the PSF is incoherent with broad spatial extent, over a range of harmonics. This "arm ordering" can be optimized for a given problem in order to maximize the spreading of the incoherent information.

In addition to non-Cartesian imaging, such as spiral imaging, THESIS is also applicable to imaging techniques that utilize Cartesian sampling, and can make use of either coherent or incoherent encoding.

For coherent encoding in Cartesian acquisitions, instead of an incoherent shifting, the nth harmonic is moved some fraction, M, of the field-of-view ("FOV") relative to the static image, such as by (n/M)×FOV. From Eqn. (2), this shift can be achieved by choosing the acquisition time, t(k), during a particular period of duration, T, to be, $$t(k) = T\left[\frac{k}{M}\%1\right]; \quad (3)$$

so that $$s(k) = \sum_{k=0}^{K-1} \sum_{n=-\infty}^{n=+\infty} S_n(x) e^{i2\pi k\left[\frac{n}{M}+\frac{x}{X}\right]}. \quad (4)$$

Figure 4:
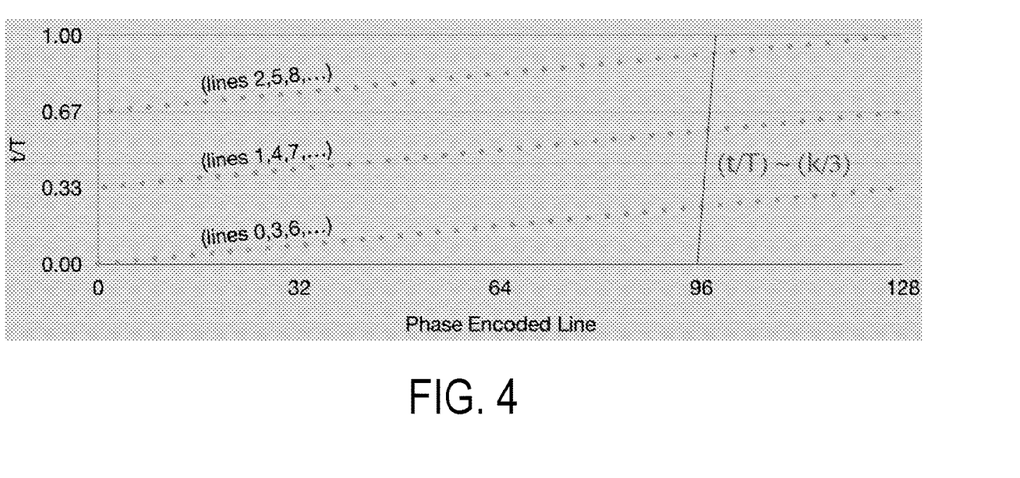
FIG. 4 shows an example shot order scheme for use with a Cartesian THESIS implementation.

Eqn. (3) can be rewritten for a particular phase encoding line, k, based on t/T, as, $$k = K\left[\frac{Mt}{T}\%1\right]. \quad (5)$$

which gives a phase encoding order like that shown in FIG. 4 for K=128 and M=3. The equation, (t/T)~(k/3), can be used with Eqn. (1) for the example shown in FIG. 4 to show that the mapping of the phase of the nth harmonic is, $$2\pi n\frac{t}{T} \to 2\pi n\frac{k}{M}; \quad (6)$$

which by the Fourier shift theorem will shift that harmonic by (n/M)×FOV in the image. To choose the phase encoding line, k, based on Eqn. (5), (t/T) should be known such that k can be dynamically chosen. This may be more challenging for oscillatory signals without a regular period, such as irregular cardiac rhythms.

Advantageously, when using coherent encoding images can be reconstructed using a non-iterative image reconstruction technique, such as GRAPPA or SENSE. For example, image reconstruction can implement the following system of equations:

$$\begin{bmatrix} D_1 \\ \vdots \\ D_L \end{bmatrix} = \begin{bmatrix} C_{1,0} & \cdots & C_{1,M-1} \\ \vdots & \ddots & \vdots \\ C_{L,0} & \cdots & C_{L,M-1} \end{bmatrix} \begin{bmatrix} I_0 \\ \vdots \\ I_{M-1} \end{bmatrix}; \quad (7)$$

where $D_i$ is the collected image from the ith coil in an RF coil array, $C_{i,j}$ is the coil sensitivity map of the ith coil circularly shifted by (j/M)×FOV in the phase encoded direction, and $I_j$ is the combination of all harmonics shifted by (j/M)×FOV in the phase encoded direction.

Figure 3:
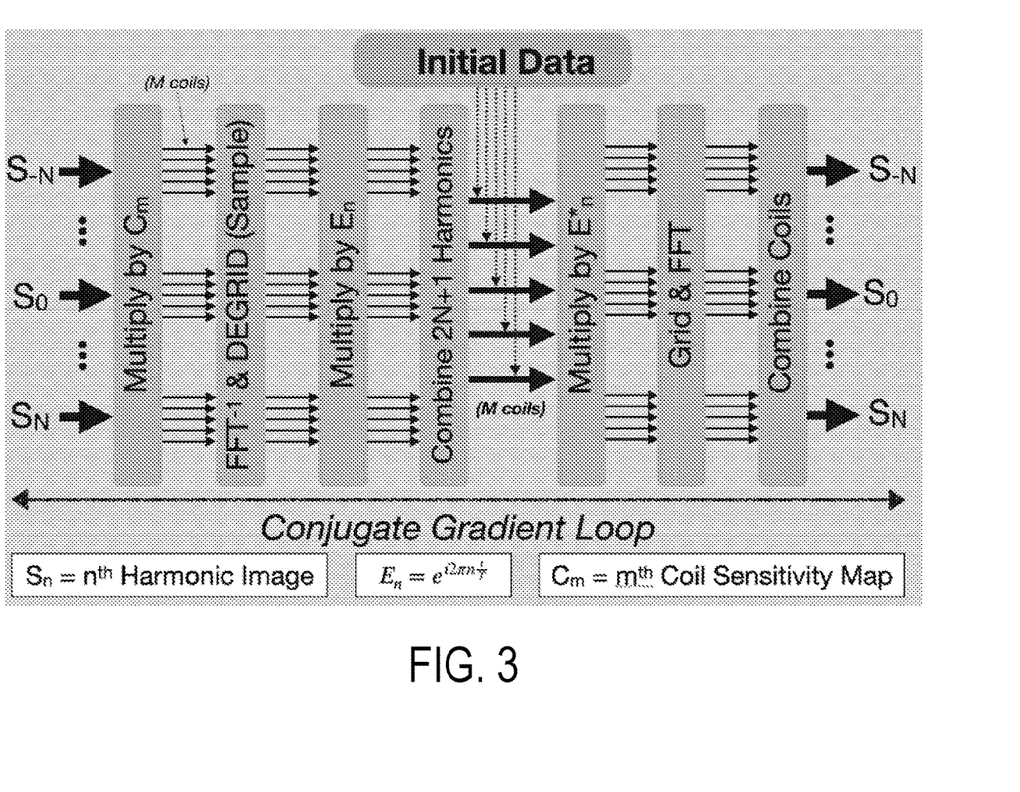
FIG. 3 illustrates an example of the computation inside of an Iterative Sense/Conjugate Gradient Loop for reconstructing spiral MRI data encoded using THESIS.

The incoherent encoding used for spiral THESIS can also be implemented with Cartesian imaging by collecting phase encoded lines in a sufficiently disordered (e.g., "pseudo-random") approach relative to (t/T), such that all harmonics except one are incoherently expressed in an image. Similar to the spiral imaging implementation, the nth harmonic can be made coherent by multiplying the phase encoded arms by $e^{-i2\pi nt(k)/T}$ before reconstruction, and a larger set of harmonics can be fully separated using an iterative approach such as the one illustrated in FIG. 37. As with the spiral imaging implementation, the phase encoding of (t/T) is preferably sufficiently random so that the incoherence produces sufficient orthogonality of the coil sensitivities to minimize any g-factor noise penalty in the final reconstruction.

In addition to the non-Cartesian (i.e., spiral) and Cartesian implementations described above, THESIS can also be implemented when signal changes inherent to the nuclear magnetic resonance ("NMR") processes themselves (e.g., T1 or T2 relaxation) are controlled, at least to some extent, by the pulse sequence. As one example, these inherent signal changes can be controlled via T2 decay during RARE, TSE, FSE, or other similar pulse sequences. As another example, these inherent signal changes can be controlled via T1 recovery during MP-RAGE or other similar pulse sequences. As still other examples, these inherent signal changes can be controlled via the migration of saturated spins due to flow, perfusion, and diffusion from ASL or other similar pulse sequences.

Advantageously, this synthetic THESIS, or SynTHESIS, technique is applicable to Cartesian and non-Cartesian (e.g., spiral) encoding schemes, using either coherent or incoherent separation of harmonics. In SynTHESIS, the signal changes are mapped to the encoding in order to simulate a pattern that can be represented by some (ideally low) number of harmonics.

Figure 5:
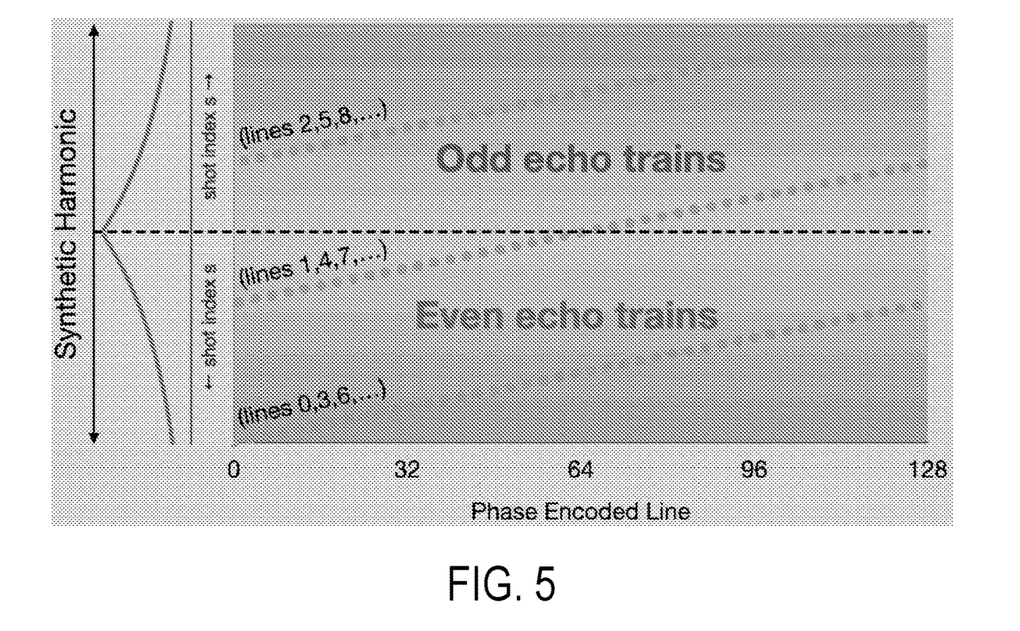
FIG. 5 shows an example shot order scheme for use with a synthetic THESIS implementation.

As a non-limiting example, SynTHESIS can be implemented using a turbo spin echo ("TSE") pulse sequence, such as RARE, with a total of L echo trains (TRs), with S shots per echo train (i.e., echo train length), such that the total phase encodings are N=S·L. The indices for trains, shots, and phase encodings can be defined as l, s, and n, respectively. Presuming an (approximate) exponential signal decay across the echo train, and if there are an even number of trains, the phase encodes, n, for even values of l can be collected as, $$n = \left[\frac{3N}{2} - M\left(1 + \frac{l+s \cdot L}{2}\right)\right] \%N; \quad (8)$$

and the phase encodes for odd values of l can be collected as, $$n = \left[\frac{N}{2} + M\left(\frac{l+s \cdot L}{2}\right)\right] \%N; \quad (9)$$

such that the T2 decay during the pulse sequence is spread across the phase encoded lines as seen in FIG. 5, which shows an example for N=128, L=8, S=16, and M=3. Collection of the data in this fashion can result in M=3 overlapping images, each shifted by FOV/3. The central image would represent the static, or non-decaying part of the signal (i.e., the zeroth harmonic) plus some small residue (+/−3rd harmonics, 6th harmonics, etc.). Application of SENSE or GRAPPA allows for this static image to be separated out, while images to either side would represent the decaying part of the signal.

Figure 6:
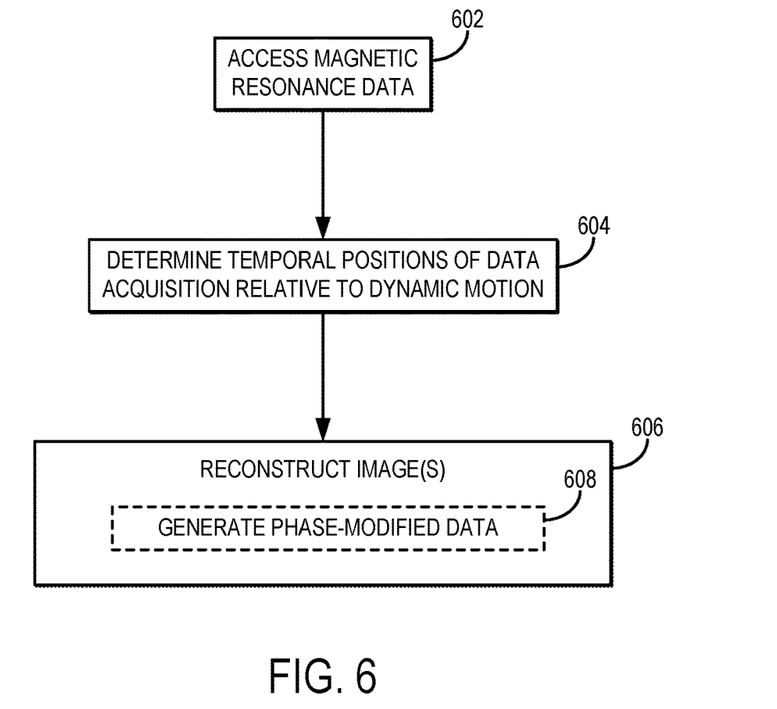
FIG. 6 is a flowchart setting forth the steps of an example method for separating static and dynamic signal components and reconstructing images of those components.

Referring now to FIG. 6, a flowchart is illustrated as setting forth the steps of an example method for separating magnetic resonance signals that are changing over a scan duration (i.e., dynamic signals) from magnetic resonance signals that are static over the same duration and generating respective images of the static and dynamic signal components. The method includes accessing magnetic resonance data with a computer system, as indicated at step 602. Accessing the data can include retrieving such data from a memory or other suitable data storage device or media. In other instances, accessing the data can include acquiring such data with an MRI system and transmitting or otherwise communicating the data to the computer system, which may be a part of the MRI system.

In general, the magnetic resonance data are acquired from a region (e.g., a slice, multiple slices, a volume) in a subject that contains both static and dynamic signal sources. For instance, the data can be acquired from a region that contains both static tissue structures and dynamic, or time-varying, tissues or other structure or sources. Examples of dynamic tissues or sources can include flowing blood, cerebrospinal fluid, cardiac motion, respiratory motion, and so on. In some embodiments, the dynamic signal sources are cyclical, which may include periodic motion. Thus, in some instances, the dynamic signal sources may have harmonic components. The dynamic motion source may also be a non-periodic motion source, such as the passage of a contrast agent (e.g., Gd-based contrast agent).

The magnetic resonance data preferably contain a number of shots. As one example, a shot may correspond to sampling a spiral trajectory in k-space. In other examples, a shot may correspond to sample a phase encoding line in k-space (e.g., a Cartesian phase encoding line) or another Cartesian or non-Cartesian k-space trajectory. The magnetic resonance data can thus be composed of a static and a number of dynamic components (e.g., harmonic components) over the set of shots.

Advantageously, the magnetic resonance data can be acquired in such a way that the components (e.g., harmonic components) of the dynamic signal are well separated. For instance, the order in which the shots are collected can be selected to optimize the dynamic signal component separation. As a non-limiting example, the acquisition order for spiral arms in a set of spiral k-space trajectories can be selected to optimize the separation of dynamic signal components. As another non-limiting example, the acquisition order of phase encoding lines in a Cartesian acquisition can be selected to optimize the separation of dynamic signal components. In either instance, the shot ordering can be selected or otherwise designed to provide either coherent or incoherent encoding.

As indicated at step 604, the temporal position of when data were acquired relative to the dynamic motion is determined. As a general example, the temporal position can indicate when during a motion cycle, which may be a periodic or harmonic motion cycle, a given shot was collected. When the dynamic motion corresponds to physiological motion (e.g., cardiac motion, respiratory motion), the temporal position indicates a time point in the physiological motion profile (e.g., cardiac cycle, respiratory cycle) when the data were acquired. In these instances, the temporal position can be determined from a measure of the physiological motion. As one example, the temporal position can be determined from a respiratory cycle signal measured with a respiratory bellows, a navigator echo, or so on. As another example, the temporal position can be determined from a cardiac cycle signal measured with an electrocardiography system.

In some instances, the temporal position can also be determined directly from the acquired data. For example, a measure from the acquired data may indicate the temporal position at which the data were acquired. As one example, a navigator echo or other reference portion of the acquired data may provide a measure of the temporal position.

As another example, the dynamic motion source can be associated with magnetization transfer implemented by applying RF pulses with a constant flip angle, but oscillating energy. In these instances, a measure of the temporal positions can be determined based on the known modulation of the RF pulses.

As still another example, the dynamic motion source can be associated with ASL tagging, in which oscillatory saturation of the arterial blood supply is produced. In these instances, a measure of the temporal positions can be determined based on the known application of the arterial saturation.

In some other instances, the dynamic motion source may be an applied vibratory stimulus used for magnetic resonance elastography ("MRE"). In these instances, data associated with the applied vibratory stimulus can be provided to determine the temporal positions at which shots of k-space data were acquired.

Images are then reconstructed from the acquired magnetic resonance data using a suitable reconstruction technique, as indicated at step 606. As a part of the image reconstruction process, phase-modified data are generated from the magnetic resonance data, as indicated at process block 608. These phase-modified data can be generated by weighting each shot in the magnetic resonance data with a corresponding phasor that describes the phase for that shot of k-space data. The phasor is constructed using the determined temporal position associated with that shot of k-space data. For example, the phasor can be constructed as $\exp(i2\pi n(t/T))$ for the nth harmonic, where t is the temporal position and T is a period of the dynamic motion source. The phase-modified data may also be generated by weighting each shot in the magnetic resonance data with a corresponding complementary phasor, which can be constructed as $\exp(-i2\pi n(t/T))$. In the example described above, the phasors are constructed using exponentials. Additionally or alternatively, other basis functions and their complementary sets (e.g., Hadamard encoding) can be used for separating the dynamic and static signals.

As one example, the reconstruction technique can include an iterative reconstruction technique, such as iterative SENSE. As another example, when the magnetic resonance data are acquired using a Cartesian sampling of k-space in such a way as to shift the dynamic component images rather than disperse them incoherently, then non-iterative reconstruction techniques, such as GRAPPA or SENSE, can provide a straightforward means of separating the signals.

The reconstructed images can include a static image that depicts separated static signal components, and one or more dynamic images that depict one or more separated dynamic signal components.

As one example, if the desired output is a static image in which flow, respiratory, or other motion-induced artifacts are removed or otherwise mitigated, then the reconstructed images can include static images that depict the static signals. In these instances, the separated dynamic signal components can be discarded or otherwise ignored.

As another example, if the desired output is one or more image that depict the dynamic motion source, then a composite image of the separated dynamic signal component images can be generated. In this example, an image is reconstructed for each separated dynamic signal component and these dynamic signal component images are combined using a weighted sum of the components images, where the weights are the respective phasors. This approach could be used, for example, to assess the dynamic components from time-of-flight imaging, or other dynamic imaging techniques. With orthogonal encoding of harmonics, there is no SNR loss for this method when looking at a single harmonic (i.e., the full SNR from the total scan time is available). However, there may be SNR loss when combining harmonics to produce cyclical motion (comparable to what is achieved when binning data).

In some implementations, a compressed sensing based reconstruction may be implemented. For instance, a form of compressed sensing can be achieved when dynamics are occurring over a limited region in space (e.g., for vascular flow) by masking the regions in each harmonic that are not contributing to that particular signal. In this way, SNR in the final image(s) can be improved.

Figure 7:
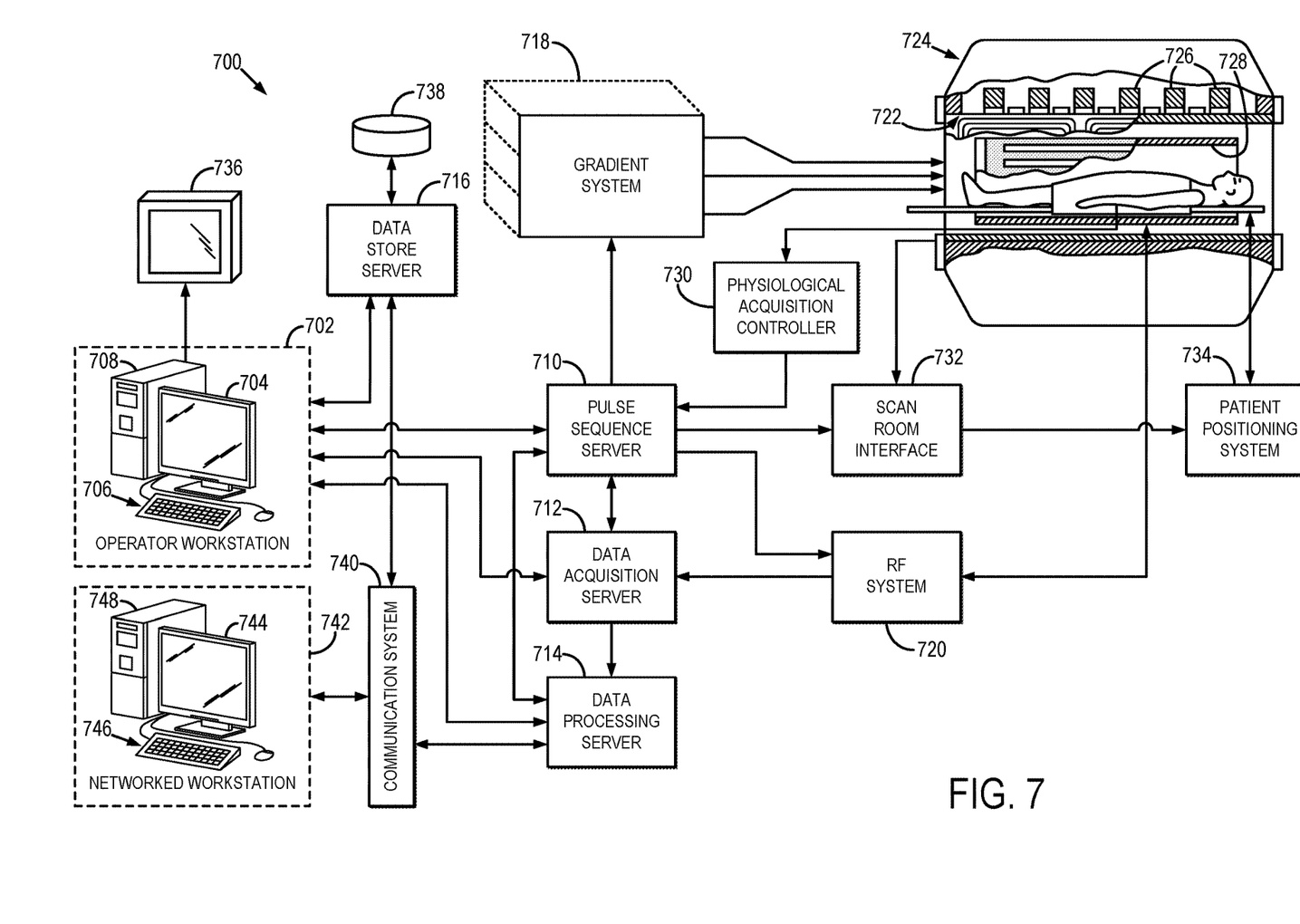
FIG. 7 is a block diagram of an example MRI system that can implement the methods described in the present disclosure.

Referring particularly now to FIG. 7, an example of an MRI system 700 that can implement the methods described here is illustrated. The MRI system 700 includes an operator workstation 702 that may include a display 704, one or more input devices 706 (e.g., a keyboard, a mouse), and a processor 708. The processor 708 may include a commercially available programmable machine running a commercially available operating system. The operator workstation 702 provides an operator interface that facilitates entering scan parameters into the MRI system 700. The operator workstation 702 may be coupled to different servers, including, for example, a pulse sequence server 710, a data acquisition server 712, a data processing server 714, and a data store server 716. The operator workstation 702 and the servers 710, 712, 714, and 716 may be connected via a communication system 740, which may include wired or wireless network connections.

The pulse sequence server 710 functions in response to instructions provided by the operator workstation 702 to operate a gradient system 718 and a radiofrequency ("RF") system 720. Gradient waveforms for performing a prescribed scan are produced and applied to the gradient system 718, which then excites gradient coils in an assembly 722 to produce the magnetic field gradients $G_x$, $G_y$, and $G_z$ that are used for spatially encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil to perform the prescribed magnetic resonance pulse sequence. Responsive magnetic resonance signals detected by the RF coil 728, or a separate local coil, are received by the RF system 720. The responsive magnetic resonance signals may be amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the prescribed scan and direction from the pulse sequence server 710 to produce RF pulses of the desired frequency, phase, and pulse amplitude waveform. The generated RF pulses may be applied to the whole-body RF coil 728 or to one or more local coils or coil arrays.

The RF system 720 also includes one or more RF receiver channels. An RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \tag{10}$$

and the phase of the received magnetic resonance signal may also be determined according to the following relationship:

$$\varphi = \tan^{-1}\left(\frac{Q}{I}\right). \tag{11}$$

The pulse sequence server 710 may receive patient data from a physiological acquisition controller 730. By way of example, the physiological acquisition controller 730 may receive signals from a number of different sensors connected to the patient, including electrocardiograph ("ECG") signals from electrodes, or respiratory signals from a respiratory bellows or other respiratory monitoring devices. These signals may be used by the pulse sequence server 710 to synchronize, or "gate," the performance of the scan with the subject's heart beat or respiration.

The pulse sequence server 710 may also connect to a scan room interface circuit 732 that receives signals from various sensors associated with the condition of the patient and the magnet system. Through the scan room interface circuit 732, a patient positioning system 734 can receive commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, so that data is not lost by data overrun. In some scans, the data acquisition server 712 passes the acquired magnetic resonance data to the data processor server 714. In scans that require information derived from acquired magnetic resonance data to control the further performance of the scan, the data acquisition server 712 may be programmed to produce such information and convey it to the pulse sequence server 710. For example, during pre-scans, magnetic resonance data may be acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also process magnetic resonance signals used to detect the arrival of a contrast agent in a magnetic resonance angiography ("MRA") scan. For example, the data acquisition server 712 may acquire magnetic resonance data and processes it in real-time to produce information that is used to control the scan.

The data processing server 714 receives magnetic resonance data from the data acquisition server 712 and processes the magnetic resonance data in accordance with instructions provided by the operator workstation 702. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 714 are conveyed back to the operator workstation 702 for storage. Real-time images may be stored in a data base memory cache, from which they may be output to operator display 702 or a display 736. Batch mode images or selected real time images may be stored in a host database on disc storage 738. When such images have been reconstructed and transferred to storage, the data processing server 714 may notify the data store server 716 on the operator workstation 702. The operator workstation 702 may be used by an operator to archive the images, produce films, or send the images via a network to other facilities.

The MRI system 700 may also include one or more networked workstations 742. For example, a networked workstation 742 may include a display 744, one or more input devices 746 (e.g., a keyboard, a mouse), and a processor 748. The networked workstation 742 may be located within the same facility as the operator workstation 702, or in a different facility, such as a different healthcare institution or clinic.

The networked workstation 742 may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742.

The present disclosure has described one or more preferred embodiments, and it should be appreciated that many equivalents, alternatives, variations, and modifications, aside from those expressly stated, are possible and within the scope of the invention.

The invention claimed is:

1. A method for reconstructing an image from magnetic resonance data, the method comprising:
    (a) accessing magnetic resonance data with a computer system, wherein the magnetic resonance data comprise k-space samples acquired from a subject with an MRI system, wherein the k-space samples were acquired in a plurality of different shots over a duration of time, wherein the k-space data include static signal components from static signal sources that are static over the duration of time and dynamic signal components from dynamic signal sources that are changing over the duration of time with a dynamic motion, wherein the dynamic signal components correspond to signal changes based on at least one of transverse relaxation or longitudinal relaxation;
    (b) determining temporal position data that defines for each of the plurality of shots temporal positions at which the k-space samples were acquired relative to the dynamic motion occurring in the duration of time;
    (c) reconstructing the image in which the static signal components and dynamic signal components are separated by:
        generating phase-modified data from the magnetic resonance data by weighting the k-space samples acquired in each of the plurality of different shots by a corresponding phasor that is constructed based in part on the temporal position corresponding to that given shot; and
        reconstructing the image from the magnetic resonance data and the phase-modified data.

2. The method as recited in claim 1, wherein the k-space samples were acquired in the plurality of different shots over the duration of time while dynamic motion is occurring in the subject.

3. The method as recited in claim 2, wherein the dynamic motion is periodic motion.

4. The method as recited in claim 3, wherein the periodic motion includes one or more harmonics.

5. The method as recited in claim 2, wherein the dynamic motion is physiological motion and the temporal position data are determined from a physiological signal measured from the subject while the magnetic resonance data were acquired.

6. The method as recited in claim 5, wherein the physiological motion is respiratory motion of the subject and the physiological signal is a respiratory cycle signal measured from the subject using respiratory bellows.

7. The method as recited in claim 5, wherein the physiological motion is cardiac motion of the subject and the physiological signal is a cardiac cycle signal measured using an electrocardiography system.

8. The method as recited in claim 1, wherein reconstructing the image comprises reconstructing the image such that static signal components in the magnetic resonance data are depicted in the image and artifacts associated with the dynamic signal components in the magnetic resonance data are mitigated in the image.

9. The method as recited in claim 1, wherein reconstructing the image comprises reconstructing a plurality of images, wherein each of the plurality of images corresponds to a different component of the dynamic motion.

10. The method as recited in claim 9, further comprising generating a composite image that depicts the dynamic motion by performing a weighted sum of the plurality of images, wherein each of the plurality of images is weighted by a corresponding one of the phasors.

11. The method as recited in claim 1, wherein the k-space samples were acquired by sampling spiral trajectories.

12. The method as recited in claim 11, wherein the order in which the spiral trajectories were sampled was selected in order to increase the separation of harmonic components of the dynamic signal components.

13. The method as recited in claim 1, wherein the temporal position data are determined based on a measure from the magnetic resonance data.

14. The method as recited in claim 1, wherein the image is reconstructed using an iterative image reconstruction technique.

15. The method as recited in claim 14, wherein the iterative image reconstruction technique is an iterative SENSE reconstruction.

16. The method as recited in claim 1, wherein each phasor is constructed using a basis function that takes as input the temporal position data.

17. The method as recited in claim 16, wherein the basis function comprises an exponential function.

18. The method as recited in claim 1, further comprising generating complementary phase-modified data by weighting the k-space samples acquired in each of the plurality of different shots by a conjugate of the corresponding complementary phasor that is constructed based in part on the temporal position corresponding to that given shot.

19. The method as recited in claim 18, wherein the phasors and conjugate phasors are constructed using a Hadamard code in order to provide a Hadamard encoding of the phase-modified data.

20. The method as recited in claim 1, wherein the magnetic resonance data were acquired using a pulse sequence that implements a plurality of echo trains, and wherein a shot order for the plurality of different shots was selected differently for even-numbered echo trains and odd-numbered echo trains.

* * * * *